United States Patent [19]

Drake et al.

[11] 4,218,394

[45] Aug. 19, 1980

[54] PREPARATION OF UNSATURATED NITRILES

[75] Inventors: Charles A. Drake; Willie W. Crouch, both of Bartlesville, Okla.

[73] Assignee: Phillips Petroleum Company, Bartlesville, Okla.

[21] Appl. No.: 32,976

[22] Filed: Apr. 24, 1979

[51] Int. Cl.² .................. C07C 120/00; C07C 121/46; C07C 121/20; C07C 121/66

[52] U.S. Cl. .............................. 260/465.8 R; 260/464; 260/465 H; 260/465 K; 260/465.9

[58] Field of Search ............. 260/464, 465.8 R, 465.9, 260/465 K, 465 H

[56] References Cited

U.S. PATENT DOCUMENTS

| | | | |
|---|---|---|---|
| B 456,900 | 2/1976 | Turk et al. | 260/465 K |
| 2,641,607 | 6/1953 | Albisetti, Jr. et al. | 260/465.3 |
| 3,035,040 | 5/1962 | Findlay | 260/34.9 |
| 3,305,600 | 2/1967 | Hopper et al. | 260/683.15 |
| 3,840,583 | 10/1974 | Turk et al. | 260/465.8 R |
| 3,883,606 | 5/1975 | Banks | 260/469.9 X |
| 3,898,268 | 8/1975 | Drake | 260/465 K X |
| 3,929,860 | 12/1975 | Drake | 260/464 X |
| 3,985,786 | 10/1976 | Drake | 260/465.8 R |
| 4,021,465 | 5/1977 | Fozzard | 260/465.8 R |
| 4,117,001 | 9/1978 | Fozzard | 260/465.9 X |
| 4,117,002 | 9/1978 | Drake | 260/465.8 R |

OTHER PUBLICATIONS

Albisetti, et al., J.A.C.S., 78 (1956), pp. 2637–2641.
Chemical Engineers Handbook, 5th Ed., pp. 4–20 and 4–21, (1973).

*Primary Examiner*—Joseph P. Brust

[57] ABSTRACT

An olefinically unsaturated nitrile, an olefinic hydrocarbon containing an allylic hydrogen and a monoadduct reaction product of an olefinic hydrocarbon and an olefinically unsaturated nitrile are contacted in a tubular reactor in the presence of a diluent to produce unsaturated dinitriles.

24 Claims, No Drawings

PREPARATION OF UNSATURATED NITRILES

This invention relates to the production of unsaturated dinitriles. In a specific aspect this invention relates to the reaction of an olefinically unsaturated nitrile, an olefinic hydrocarbon and a monoadduct of an olefinic hydrocarbon and an olefinically unsaturated nitrile in a tubular reactor in the presence of a diluent to yield olefinically unsaturated dinitrile products having a greater number of carbon atoms than the unsaturated nitrile reactant.

In U.S. Pat. No. 2,641,607 (issued June 9, 1953), Albisetti et al describe the thermal reaction of a 2-alkenenitrile (e.g., acrylonitrile) with a neutral olefinic compound (e.g., isobutylene) in a first stage reaction to produce unsaturated mononitriles having a greater number of carbon atoms (e.g., 5-methyl-5-hexenenitrile). Albisetti et al, state that the reaction effluent can be distilled to recover the unsaturated mononitrile product, and that the recovered unsaturated mononitrile product can be thermally reacted with a neutral olefinic compound in a second stage reaction to produce unsaturated dinitriles. The patentees state that the first stage reaction can be conducted in the presence or absence of an inert diluent or solvent. The patent lists hydrocarbons, ethers and esters as suitable inert organic solvents, and then states that the reaction also takes place in the presence of water as a diluent, the water serving as a heat transfer medium.

In J. Am. Chem. Soc. 78, pp. 2637-2641 (1956), Albisetti et al, describe further work with the thermal reaction of a 2-alkenenitrile with a neutral olefinic compound in a first stage and the subsequent reaction in a second stage of a neutral olefinic compound with the reaction product of the first stage to produce unsaturated dinitriles. The authors state that water can be employed as the reaction medium in the second stage reaction of acrylonitrile with 5-methyl-5-hexenenitrile to produce 5-methylenenonanendinitrile. The authors also state that in the case of polymerizable nitriles, the use of water as the medium prevented formation of tars.

In U.S. Pat. No. 3,840,583 (issued Oct. 8, 1974) Turk et al, disclose that the yield of unsaturated dinitriles can be increased by contacting an unsaturated mononitrile, an olefin and a monoadduct reaction product of an unsaturated mononitrile and an olefin wherein the monoadduct reaction product is present in significant amount during substantially the entire reaction period. The patentees stated that this single stage reaction could be carried out in the presence or absence of a solvent or diluent which is nonreactive with either the reactants or the reaction products. The patentees list various hydrocarbons various ethers, tetrahydrofuran, dioxane, carbon tetrachloride and methylene chloride as representative commercially available nonreactive solvents that can be employed.

In U.S. Pat. No. 3,985,786 (issued Oct. 12, 1976) Drake discloses that the utilization of an aqueous medium as the diluent in the Turk et al, single stage process provides a greater increase in the yield of unsaturated dinitriles than would be expected from the summation of the increase in yield in unsaturated dinitriles achieved by the utilization of water as the diluent in both stages of the Albisetti et al, process and the increase in yield in unsaturated dinitriles achieved by the utilization of the Turk et al, single stage reaction instead of the Albisetti et al two-stage process.

In the past the reactions described in the referenced patents and publication appear to have been carried out in conventional agitated tank-type reactors. It has now been discovered that the use of a tubular reactor in Turk et al, and Drake single stage processes provides an increase in the yield of unsaturated dinitriles, increased percentage conversion of the reactants, decreased production of undesired heavy products and reduced reactor fouling.

Accordingly, it is an object of this invention to provide an improved process for the reaction of an olefinic hydrocarbon and an olefinically unsaturated nitrile in order to obtain an olefinically unsaturated dinitrile reaction product having a greater number of carbon atoms than the original nitrile. Another object is to provide an improved process which results in increased yields of high carbon number olefinically unsaturated dinitrile reaction products. Another object of the invention is to increase the percentage conversion of the reactants. A further object of the invention is to decrease the production of undesired heavy products. Yet another object of this invention is to reduce reactor fouling. Other objects, aspects and advantages of the invention will be apparent study of the specification and the appended claims to the invention.

Any unsaturated mononitrile can be employed in the practice of this invention provided the mononitrile contains ethylenic unsaturation, contains at least one hydrogen atom attached to a doubly bonded carbon atom, and contains a cyano group attached to a carbon atom adjacent and doubly bonded to a carbon atom which is attached to at least one hydrogen atom. Preferably the mononitrile reactant is free of acetylenic unsaturation and contains from 1 to 2 ethylenically unsaturated, non-conjugated double bonds as the sole aliphatic unsaturation, while the total number of carbon atoms in the mononitrile reactant is within the range of 3 to 18, more preferably within the range of 3 to 8. Illustrative unsaturated mononitrile reactants include those represented by the formula

$$RCH=CR-CN$$

wherein each R is independently selected from the group consisting of hydrogen and hydrocarbyl radicals. Preferably the hydrocarbyl radicals are selected from the group consisting of alkyl, cycloalkyl, and aryl hydrocarbyl radicals and combinations thereof, for example alkylcycloalkyl, cycloalkylalkyl, aralkyl and arylcycloalkyl radicals. Examples of unsaturated nitriles meeting the requirements, of the above formula are acrylonitrile, methacrylonitrile, 2-decenenitrile, 3-cyclohexyl-2-propenenitrile, 4-phenyl-2butenenitrile, 3(p-toyl)-2-propenenitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, 5-p-tolyl-2-nonenenitrile, and the like, and mixtures thereof.

Any acyclic or cyclic olefinic hydrocarbon compound can be employed in the practice of this invention, provided that the compound has at least one olefinic linkage having joined to one of the doubly bonded carbons a carbon atom having at least one hydrogen atom attached thereto, said doubly bonded carbon atoms being free or cyano groups attached thereto. The olefinic hydrocarbons preferably are free of acetylenic unsaturation and have from 3 to 18 carbon atoms per molecule with from 1 to 2 ethylenically unsaturatd, nonconjugated double bonds as the sole aliphatic unsaturation. The preferred types of these compounds are the open chain monoolefinic hydrocarbons represented by the formula $$R'_2C=CR'-CHR'_2$$

wherein each R' is independently selected from the group consisting of hydrogen and hydrocarbyl radicals, said hydrocarbyl radicals being selected from the group consisting of alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of olefinically unsaturated hydrocarbon compounds which are useful in the process of this invention include propylene, isobutylene, diisobutylene, triisobutylend, 1,5-hexadiene, beta-pinene, 1,5-cyclooctadiene, 2,4,4-trimethyl-1-pentene, 2-butene, biallyl, bimethallyl, alpha-methylstyrene, beta-methylstyrene, 1-pentene, 1-decene, cyclohexene, 1-allylcyclohexene, 3-allylcyclohexene, 4-allylcyclohexene, allylbenzene, 3,4,4-trimethyl-2-pentene, 1-dodecene, 2,3-dimethyl-2-butene, and 2-methyl-1-phenyl-2-propene, and the like, and mixtures of any two or more thereof.

Suitable monoadduct reactants include any monoadduct reaction product of an olefinic hydrocarbon, as hereinabove defined, and an unsaturated mononitrile, as hereinabove defined. It is believed that the olefinic hydrocarbon compound and the unsaturated mononitrile react in accordance with the "ene" reaction to produce, as the principal monoadduct reaction product, a compound having the structural formula

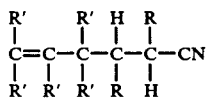

Generally, a lesser amount of an isomeric monoadduct reaction product having the formula

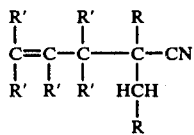

is also produced. Thus, isobutylene and acrylonitrile react to produce 5-methyl-5-hexenenitrile as the principal monoadduct reaction product along with a small amount of 2,4-dimethyl-4-pentenenitrile. It can be readily seen that isobutylene as the olefinic hydrocarbon reactant possesses six of the required allylic hydrogens but that all six are structurally equivalent so that only two monoadduct reaction compounds corresponding to the above general formulas are produced according to the "ene" reaction.

However, it will also be evident that if a compound having two or more allylic hydrogens which are not structurally equivalent is employed as the olefinic hydrocarbon reactant, the number of expected isomeric monoadduct reaction product compounds having the above general formulas will be increased. For example, if 2,4,4-trimethyl-1-pentene is reacted with acrylonitrile the major monoadduct reaction products expected according to the "ene" reaction would be 5-methylene-7,7-dimethyloctanenitrile and 4-methylene-2,6,6-trimethylheptanenitrile with lesser amounts of 5,7,7-trimethyl-5-octenenitrile and 4-t-butyl-5-methyl-5-hexenenitrile. Other factors, not fully understood at present, may influence the relative amounts of the possible isomers in the monoadduct reaction product and in other instances presently employed analytical methods may not distinguish the various isomers present. Indeed, the monoadduct reaction product finds utility in many applications with no need of a costly separation of the isomers present in the monoadduct reaction product. The isomeric mixture reaction product produced by the reaction of an olefinic hydrocarbon and an olefinically unsaturated nitrile can be employed as the monoadduct reactant, or one or more isomers can be separated from the isomeric mixture reaction product and such separated isomer or isomers can be employed as the monoadduct reactant. Examples of suitable monoadduct reactants include 5-methyl-5-hexenenitrile, 3,5-dimethyl-5-hexenenitrile, 3-(n-propyl)-5-hexenenitrile, 3-(n-propyl)-6-phenyl-5-hexenenitrile, 2,4-dimethyl-4-pentenenitrile, 2-ethyl-4-methyl-4-pentenenitrile, 2(n-butyl)-4-pentenenitrile, 2-(n-butyl)-5-phenyl-4-pentenenitrile, and mixtures of any two or more thereof.

The diadduct reaction products obtained by the process of this invention comprise the reaction product mixtures formed by the monoaddition of an unsaturated mononitrile and any monoadduct reaction product. Exemplary of a diadduct reaction product is the reaction product mixture comprising the major isomer species 5-methylenenonanedinitrile and 5-methyl-4-nonenedinitrile, and minor isomer species 2-methyl-4-methyleneoctanedinitrile, 2,4-dimethyl-4-octenedinitrile, 2,4-dimethyl-3-octenedinitrile, 2,6-dimethyl-4-methyleneheptanedinitrile and 2,4,6-trimethyl-3-heptenedinitrile.

Any amount of olefinic hydrocarbon, olefinically unsaturated mononitrile and monoadduct reaction product can be employed in the practice of this invention. In general, the mol ratio of olefinically unsaturated mononitrile reactant to olefinic hydrocarbon reactant will be in the range of about 10:1 to about 1.1:1, preferably in the range of about 2:1 to about 0.3:1. In general, the monoadduct reaction product will be employed in an amount such that, at any point in the tubular reactor, the net monoadduct reaction product present in the reaction mixture will constitute from about 10 to about 90, preferably from about 20 to about 80, and more preferably from about 30 to about 70 weight percent of the total reaction mixture. The net amount of monoadduct reaction product present in the tubular reactor is the sum of the amount of monoadduct reaction product charged to the tubular reactor plus the amount of monoadduct reaction product produced by the reaction of the olefinic hydrocarbon reactant and the olefinically unsaturated mononitrile reactant in the tubular reactor less the monoadduct reaction product consumed by reaction with the olefinically unsaturated mononitrile in the tubular reactor to produce diadduct. The monoadduct reaction product charged to the tubular reactor can be the same as or different from the monoadduct reaction product produced by the reaction of the olefinic hydrocarbon reactant and the olefinically unsaturated mononitrile reactant in the tubular reactor, but it will be generally preferred for them to be the same. The total reaction mixture includes all fluid materials present in the tubular reactor, i.e., reactants, diluents, products, byproducts, etc.

Any suitable tubular reactor can be employed in the practice of the invention. The tubular reactor may be constructed of either a single continuous conduit or several conduits in parallel. The reactants enter at one end of the tubular reactor and the products leave from the other end of the tubular reactor. Thus, there is a continuous variation in the composition of the reacting mixture throughout the length of the tubular reactor. Heat transfer to or from the tubular reactor may be accomplished by means of a jacket or a shell and tube design.

The tubular reactor is characterized by operation under plug flow conditions. Operation under plug flow conditions assures complete mixing in the radial direction and no diffusion in the flow direction (back-mixing). As a result the velocity, temperature and composition profiles are substantially flat over any cross-sectional area perpendicular to the flow but the composition varies along the flow path.

Any suitable dimensions for the tubular reactor may be employed in the practice of the invention. A tubular reactor will generally have a length to diameter ratio of at least 20:1. Turbulent mixing in the radial direction is highly desirable in the present invention but streamline flow may be utilized if desired. It is well known, that when the Reynolds number exceeds approximately 2100, turbulent mixing prevails. The Reynolds number ($N_{RE}$) is defined as:

$$N_{RE} = DV\rho/\mu \qquad 1$$

where
D = inside diameter of the tubular reactor;
V = linear velocity of reactants;
$\rho$ = density of reactants; and
$\mu$ = viscosity of the reactants.

It is thus preferred that the dimensions of the tubular reactor be such as to give a Reynolds number greater than 2100 under the operating conditions for the tubular reactor. However, the invention is applicable to tubular reactors having lower Reynolds numbers.

Any suitable reaction conditions for a continuous process can be employed in the practice of the invention. The reaction time employed in the practice of this invention can vary widely. The liquid hourly space velocity will generally be in the range of about 0.05 to about 20, preferably in the range of about 0.1 to about 10, more preferably in the range of about 0.5 to about 2.

The reaction temperatures that can be employed in the practice of the invention can vary widely. Generally, however, suitable reaction temperatures are within the range of from about 100° C. to about 500° C., and preferred reaction temperatures are within the range of from about 200° C. to about 350° C. The temperature will generally be substantially uniform along the length of the tubular reactor.

The reaction pressures suited to the practice of this invention also vary widely. Reaction pressures within a range of from about atmospheric pressure to about 100,000 psig can be employed; however, reaction pressures within the range of from about 500 psig to about 4000 psig are preferably employed.

If desired, the processes of this invention can be carried out in the presence of a polymerization inhibitor. The use of the inhibitor often advantageously limits side reactions such as the dimerization or polymerization of the olefinically unsaturated mononitrile. When an inhibitor is employed, it is generally desirable that an amounnt of from about 0.001 to about 5, preferably from about 0.1 to about 1, percent by weight inhibitor based on the weight of unsaturated mononitrile reactant be employed. Suitable inhibitors include hydroquinone, 2,6-di-tert-butyl-para-cresol, 2,6-di-tert-butylhydroquinone, 4-tert-butylcatechol, para-hydroxydiphenylamine, and the like, and mixtures of any two or more thereof.

The reaction of the above described olefinic hydrocarbon reactant, olefinically unsaturated mononitrile reactant and monoadduct reaction product reactant may be carried out in the presence of any suitable diluent. Preferably the diluent comprises at least 50 weight percent water, more preferably at least 80 weight percent water, and more preferably consisting essentially of water. The codiluent with water, if employed, can be any solvent or diluent which is nonreactive with either the reactants or the reaction products. Examples of suitable codiluents include benzene, toluene, paraxylene, ortho-xylene, met-xylene, ethylbenzene, diethyl ether, ethyl propyl ether, dibutyl ether, tetrahydrofuran, dioxane, cyclohexane, carbon tetrachloride, methylene chloride, and the like, and mixtures of any two or more thereof.

The diluent can be employed in any suitable amount. In general the diluent will be employed in an amount in the range of about 0.01 to about 40 parts by weight of total diluent per part by weight of olefinically unsaturated mononitrile reactant charged to the reaction zone. The amount of diluent currently preferred is in the range of about 0.1 to about 20 parts by weight of total diluent per part by weight of olefinically unsaturated mononitrile reactant charged to the reaction zone. The advantages of the preferred aqueous diluent system include improved selectivity to the desired olefinically unsaturated nitrile and reduced amounts of heavy polymeric byproduct. This latter byproduct is particularly objectionable because it tends to foul reactor surfaces.

A convenient method of carrying out this invention comprises combining a mixture of an olefinically unsaturated mononitrile (e.g., acrylonitrile), an olefinic hydrocarbon compound (e.g., isobutylene), and a monoadduct reaction product reactant (e.g., a mixture of 5-methyl-5-hexenenitrile and 2,4-dimethyl-4-pentenenitrile) with a diluent fluid (water) and then introducing the combined mixture of reactants and diluent fluid into a heated tubular reactor. The temperature is maintained within the range of about 200° to about 250° C.; the pressure is maintained from about 500 to about 4000 psig; the mol ratio of the olefinically unsaturated mononitrile to the olefinic hydrocarbon is maintained in the range of about 5:1 to about 0.2:1; the concentration of the monoadduct reaction product in the reaction mixture is maintained in the range of about 20 to about 80 weight percent; and the liquid hourly space velocity is maintained in the range of about 0.5 to about 2. The resulting olefinically unsaturated dinitrile reaction product which is removed from the product end of the tubular reactor is readily isolated from the reaction effluent mixture by any convenient product recovery method such as fractional distillation.

If desired, the reaction can be carried out in the presence of any suitable promoter, for example an organo derivative of a Group VA element defined by the following formula $R'''_nZH_{3-n}$ wherein each R''' is independently selected from the group consisting of aryl, alkaryl, cycloalkylaryl, araryl, aryloxy, alkaryloxy, arylaryloxy; wherein each R''' group contains from 6 to 12 carbon atoms; Z is selected from the group consisting of N, P, P=O, As, Sb, or Bi; and n is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, diphenyl-4-biphenylphosphine, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures thereof. The variant designated by n in mixtures of promoters represented by the formula $R'''_nZH_{3-n}$ can vary, with the arithmetical sum of the value of n of individual promoters, from 2 to 3. The term "reaction promoting material" includes materials commonly called catalysts as well as materials commonly called promoters.

If employed, the amount of promoter utilized in the process of this invention can vary widely. In general, the mol ratio of promoter to unsaturated mononitrile reactant charged to the tubular reactor would be in the range of about 1:20 to about 1:1. Preferably, the mol ratio of promoter to unsaturated mononitrile reactant charge would be in the range of about 1:10 to about 1:3.

The following examples are presented in further illustration of the invention but should not be unduly construed in limitation thereof.

EXAMPLE I

The following runs were conducted to illustrate the influence of reactor type on conversion, yield and reactor productivity. All runs were conducted at a reaction temperature of 280° C., pressure of 2500 psig (17 MPa) and reactor residence time of 0.6 hour. The approximate composition (weight percent) of the organic feed was:

| Acrylonitrile (ACN) | 13 eight percent |
| isobutylene | 24 weight percent | monoadduct (MA) mixture of approximately 95 weight per c..nt 5-methyl-5-hexene-itrile with approximately 5 weight percent 2,4-dimethyl-4-pentenenitrile    63 weight percent Sufficient water was added to maintain a water/acrylonitrile weight ratio of 1.3. The isobutylene/monoadduct weight ratio was 0.75.

Runs 1 and 2 were conducted utilizing a 500 ml autoclave reactor which is considered a tank-type reactor. In run 1 the agitator associated with the autoclave reactor was operated at 2000 rpm. In run 2 the agitator associated with the autoclave reactor was not operated. Run 3 was conducted in a 0.18 inch inside diameter, 60 foot long stainless steel tubular reactor. The tubular reactor was coiled and immersed in a hot oil bath. The tubular reactor was operated at a Reynolds number of 200 which implies streamline flow rather than turbulent flow. A tubular reactor having turbulent flow is not practical on a laboratory scale. All runs were continuous, with data taken after the reactor had been lined out under simulated recycle conditions with return of the monoadduct to the reactor. The yield of monoadduct was obtained by subtracting the monoadduct fed into the tubular reactor from the monoadduct in the effluent flowing from the tubular reactor. Ideally, the net yield of monoadduct should be zero; however, this was not quite achieved in the first two runs.

The important benefits illustrated by Table I are the improved acrylonitrile (ACN) conversion and increased reactor productivity. Additionally, it has been found that the tubular reactor remains virtually free of fouling after extended operation whereas the agitated reactor did exhibit some fouling tendencies, and had to be cleaned out frequently. The nonagitated operation of run 2 indicates that the reactor contents must be essentially homogeneous since performance was not adversely affected by the lack of agitation. In fact, performance was slightly improved. This may be due to reduced short-circuitig in the nonagitated reactor, since reactants were introduced at the bottom of the reactor and product removed at the top.

It is believed that much of the benefit gained from the use of a tubular reactor, as illustrated in Table I, is gained because at reactor conditions the reactor contents may be in a supercritical state. The reactor contents are thus essentially homogeneous which means that agitation is of no value. The plug flow which can be obtained in a tubular reactor virtually eliminates backmixing thereby aiding in improved conversion as is illustrated in Table I.

TABLE I

| Run No. | Reactor Type | ACN Converted, % | Yield Based on ACN Converted, % | | | | | Reactor Productivity, Kg/m³ . s |
|---|---|---|---|---|---|---|---|---|
| | | | MA | Byproduct | DA | MA + DA | Heavies | |
| 1 | Stirred Autoclave | 47.1 | 2.5 | 3.8 | 84.1 | 86.6 | 10.3 | 0.020 |
| 2 | Nonstirred Autoclave | 52.8 | 2.8 | 3.4 | 83.3 | 86.1 | 11.0 | 0.021 |
| 3 | Tubular | 56.4 | 0.0 | 2.5 | 84.1 | 84.1 | 10.6 | 0.023 |

EXAMPLE II

A series of runs were made in the tubular reactor described in Example I and used for run 3 to study the effects of reactor variables. The results of these runs are illustrated in Table II.

TABLE II

| Run MA No. | Reactor Temp., °C. | Reactor Pressure (psig) | Residence Time, Hr. | H₂O-/ACN, Wt. Ratio | iC₄= /ACN, Wt. Ratio | ACN Converted, % | Yield Based on ACN Converted, % | | | | Reactor Productivity, Kg/m³·s |
|---|---|---|---|---|---|---|---|---|---|---|---|
| | | | | | | | MA | Byproduct | DA | Heavies | |
| 4 | 280 | 2500 | 0.60 | 0.69 | 1.3 | 55.9 | 2.0 | 2.4 | 79.0 | 9.6 | 0.68 |
| 5 | 280 | 2500 | 0.45 | 0.82 | 1.3 | 49.1 | 4.2 | 2.6 | 80.7 | 9.4 | 0.80 |
| 6 | 280 | 2500 | 0.60 | 0.71 | 1.3 | 56.4 | 0 | 2.5 | 84.1 | 10.6 | 0.70 |
| 7 | 280 | 2500 | 0.67 | 0.71 | 1.3 | 67.0 | 3.0 | 2.4 | 79.4 | 11.7 | 0.69 |
| 8 | 280 | 2500 | 0.40 | 0.71 | 1.3 | 49.3 | 12.4 | 2.6 | 73.6 | 11.0 | 0.80 |
| 9 | 280 | 2000 | 0.45 | 0.71 | 1.3 | 47.4 | 8.5 | 2.4 | 77.1 | 10.8 | 0.69 |
| 10 | 280 | 1500 | 0.45 | 0.71 | 1.3 | 43.3 | 5.3 | 3.4 | 74.1 | 11.8 | 0.60 |
| 11 | 280 | 2500 | 0.30 | 0.71 | 1.3 | 43.5 | 8.2 | 2.5 | 81.0 | 11.0 | 1.03 |
| 12 | 280 | 2500 | 0.20 | 0.71 | 1.3 | 32.4 | 8.0 | 3.0 | 76.0 | 11.7 | 1.08 |
| 13 | 290 | 2500 | 0.30 | 0.71 | 1.3 | 57.0 | 10.1 | 2.5 | 67.7 | 13.3 | 1.13 |
| 14 | 280 | 2500 | 0.30 | 0.71 | 1.0 | 44.0 | 7.9 | 2.4 | 75.7 | 11.5 | 0.98 |
| 15 | 280 | 2500 | 0.60 | 0.71 | 2.6 | 57.5 | 5.1 | 3.1 | 83.4 | 8.1 | 0.69 |
| 16 | 280 | 2500 | 0.60 | 0.71 | 0.7 | 69.6 | 5.2 | 2.7 | 84.0 | 11.1 | 0.87 |
| 17 | 280 | 2500 | 0.60 | 0.71 | 3.9 | 54.8 | 0.6 | 4.2 | 87.3 | 7.2 | 0.71 |
| 18 | 280 | 2500 | 0.60 | 0.71 | 0.3 | 73.1 | 3.2 | 3.5 | 79.9 | 15.2 | 0.86 |
| 19 | 270 | 2500 | 0.60 | 0.71 | 1.3 | 49.9 | 2.9 | 2.9 | 86.0 | 9.4 | 0.64 |
| 20 | 290 | 2500 | 0.60 | 0.71 | 1.3 | — | −3.4 | 3.7 | 81.1 | 13.3 | 0.85 |

The general conclusions that may be drawn from the data set forth in Table II are as follows:

(1) Reactor temperature of 280° C. is near optimum. Higher temperatures give better productivity but higher yield of heavy byproducts while lower temperatures result in lower productivity and lower yield of heavies.

(2) Short residence time increases reactor productivity but reduces conversion and favors the production of monoadduct.

(3) Higher H₂O/ACN ratios favor increased selectivity to diadduct but reduces ACN conversion and reactor productivity.

(4) Reactor pressure of 2500 psig is near optimum. Reduced pressure resulted in reduced acrylonitrile conversion, reduced reactor productivity and increased production of heavies.

Reasonable variations and modifications are possible within the scope of the foregoing disclosure and the appended claims to the invention.

That which is claimed is:

1. A process which comprises contacting at least one olefinic hydrocarbon reactant, at least one olefinically unsaturated mononitrile reactant and at least one monoadduct reaction product of an olefinic hydrocarbon compound and an olefinically unsaturated mononitrile compound, in a tubular reactor in the presence of a diluent, under reaction conditions suitable to produce at least one olefinically unsaturated dinitrile product, each of said olefinically unsaturated mononitrile reactant and said olefinically unsaturated mononitrile compound containing at least one hydrogen atom attached to a doubly bonded carbon atom and containing a cyano group attached to a carbon atom adjacent and doubly bonded to a carbon atom which is attached to at least one hydrogen atom, each of said olefinic hydrocarbon reactant and said olefinic hydrocarbon compound having at least one olefinic linkage having joined to one of the doubly bonded carbons a carbon atom having at least one hydrogen atom attached thereto, wherein at substantially any point in said tubular reactor the concentration of said monoadduct reaction product in the resulting reaction mixture is within the range of about 10 to about 90 weight percent of the total reaction mixture.

2. A process in accordance with claim 1 wherein said tubular reactor is operated under plug flow conditions.

3. A process in accordance with claim 2 wherein said tubular reactor comprises a single, elongated conduit means.

4. A process in accordance with claim 2 wherein said tubular reactor comprises a plurality of elongated conduit means.

5. A process in accordance with claim 1 wherein each of said at least one olefinic hydrocarbon reactant and said olefinic hydrocarbon compound is free of acetylene unsaturation and has from 3 to 18 carbon atoms per molecule with from 1 to 2 ethylenically unsaturated, nonconjugated double bonds as the sole aliphatic unsaturation.

6. A process in accordance with claim 5 wherein each of said at least one olefinically unsaturated mononitrile compound is free of acetylenic unsaturation, has from 1 to 2 ethylenically unsaturated, nonconjugated double bonds as the sole aliphatic unsaturation, and has from 3 to 18 carbon atoms per molecule.

7. A process in accordance with claim 6 wherein each of said at least one olefinic hydrocarbon reactant and said olefinic hydrocarbon compound is represented by the formula R′₂C=CR′—CHR′₂, wherein each R′ is independently selected from the group consisting of hydrogen and hydrocarbyl radicals; and wherein each of said at least one olefinically unsaturated mononitrile reactant and said olefinically unsaturated mononitrile compound is represented by the formula RCH=CR—CN wherein each R is independently selected from the group consisting of hydrogen and hydrocarbyl radicals.

8. A process in accordance with claim 7 wherein said reaction conditions comprise a temperature in the range of about 240° C. to about 350° C., a pressure in the range of about 1000 to about 4000 psig, and a mole ratio of said olefinically unsaturated mononitrile reactant to said olefinic hydrocarbon reactant in the range of about 5:1 to about 0.2:1; and wherein said at least one monoadduct reaction product comprises compounds having the structural formula

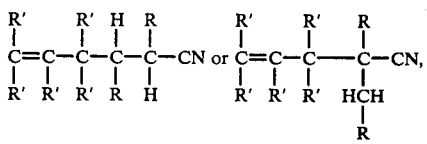

wherein R and R' are as defined above; and further comprising recovering from the resulting reaction effluent said at least one olefinically unsaturated dinitrile reaction product.

9. A process in accordance with claim 7 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

10. A process in accordance with claim 9 wherein said diluent comprises at least 50 weight percent water; the balance, if any, of said diluent being nonreactive with the reactants and the reactant products.

11. A process in accordance with claim 10 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

12. A process in accordance with claim 10 wherein at substantially any point in said tubular reactor said concentration of monoadduct reaction product in said reaction mixture is maintained within the range of about 20 to about 80 weight percent.

13. A process in accordance with claim 12 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

14. A process in accordance with claim 1 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1.

15. A process in accordance with claim 1 wherein each of said at least one olefinic hydrocarbon reactant and said olefinic hydrocarbon compound has from 3 to 18 carbon atoms and is represented by the formula R'$_2$C=CR'—CHR'$_2$, wherein each R' is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula RCH=CR—CN wherein each R is independently selected from the group consisting of hydrogen and hydrocarbyl radicals.

16. A process in accordance with claim 15 wherein said reaction conditions comprise a temperature in the range of about 100° C. to about 500° C., a pressure in the range of about atmospheric to about 100,000 psig, and a mole ratio of said olefinically unsaturated mononitrile reactant to said olefinic hydrocarbon reactant in the range of about 10:1 to about 0.1:1; and wherein said diluent comprises at least 50 weight percent water; the balance; if any, of said diluent being nonreactive with the reactants and the reaaction products,; the amount of said diluent being in the range of about 0.01 to about 40 parts by weight per part by weight of said at least one olefinically unsaturated mononitrile reactant.

17. A process which comprises contacting at least one olefinic hydrocarbon reactant, at least one olefinically unsaturated olefinic hydrocarbon reactant, at least one olefinically unsaturated mononitrile reactant and at least one monoadduct reaction product of an olefinic hydrocarbon compound and an olefinically unsaturated mononitrile compound in a tubular reactor in the presence of a diluent, under reaction conditions suitable to produce at least one olefinically unsaturated dinitrile product;

wherein each of said at least one olefinic hydrocarbon reactant and said olefinic hydrocarbon compound has from 3 to 18 carbon atoms and is represented by the formula R'$_2$C=CR'—CHR'$_2$, wherein each R' is independently selected from the group consisting of hydrogen and hydrocarbyl radicals; and wherein each of said at least one olefinically unsaturated mononitrile reactant and said olefinically unsaturated mononitrile compound has from 3 to 18 carbon atoms and is represented by the formula RCH=CR—CN, wherein each R is independently selected from the group consisting of hydrogen and hydrocarbyl radicals;

wherein said at least one monoadduct rection product comprises compounds having the structural formula

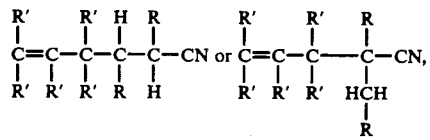

wherein R and R' are as defined above;
wherein said at least one olefinically unsaturated dinitrile product is formed by the monoaddition of a said olefinically unsaturated mononitrile reactant and said monoadduct reaction product;
wherein the amount of said diluent is in the range of about 0.01 to about 40 parts by weight per part by weight of said at least one olefinicaily unsaturated mononitrile reactant;
wherein said reaction conditions comprise a temperature in the range of about 100° C. to about 500° C., a pressure in the range of about atmospheric to about 100,000 psig, and a liquid hourly space velocity in the range of about 0.05 to about 20;
wherein the mol ratio of said at least one olefinically unsaturated mononitrile reactant to said at least one olefinic hydrocarbon reactant is in the range of about 10:1 to about 0.1:1; and
wherein at substantially any point in said tubular reactor the concentration of said monoadduct reaction product in the resulting reaction mixture is within the range of about 10 to about 90 weight percent of the total reaction mixture.

18. A process in accordance with claim 17 wherein said tubular reactor is operated under plug flow conditions.

19. A process in accordance with claim 18 wherein said tubular reactor comprises a single, elongated conduit means.

20. A process in accordance with claim 18 wherein said tubular reactor comprises a plurality of elongated conduit means.

21. A process in accordance with claim 17 wherein said diluent comprises at least 50 weight percent water; the balance, if any, of said diluent being nonreactive with the reactants and the reactant products.

22. A process in accordance with claim 17 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

23. A process in accordance with claim 22 further comprising recovering from the resulting reaction effluent said at least one olefinically unsaturated dinitrile reaction product.

24. A process in accordance with claim 17 wherein said at least one olefinically unsaturated mononitrile reactant is acrylonitrile, wherein said olefinically unsaturated mononitrile compound is acrylonitrile, wherein said at least one olefinic hydrocarbon reactant is isobutylene, and wherein said olefinic hydrocarbon compound is isobutylene.

* * * * *

UNITED STATES PATENT AND TRADEMARK OFFICE
CERTIFICATE OF CORRECTION

PATENT NO. : 4,218,394
DATED : August 19, 1980
INVENTOR(S) : Charles A. Drake

It is certified that error appears in the above—identified patent and that said Letters Patent are hereby corrected as shown below:

Column 12, claim 17, line 9, after "unsaturated", delete "olefinic hydrocarbon reactant, at least one olefinically unsaturated".

Signed and Sealed this

Twenty-first Day of July 1981

[SEAL]

Attest:

GERALD J. MOSSINGHOFF

Attesting Officer     Commissioner of Patents and Trademarks